United States Patent [19]

Krause et al.

[11] Patent Number: 5,455,177
[45] Date of Patent: Oct. 3, 1995

[54] METHOD FOR ANALYSIS OF A MEDICAL SAMPLE

[75] Inventors: Friedemann Krause, Feldafing; Andreas Gfrörer, Starnberg, both of Germany

[73] Assignee: Boehringer Mannheim GmbH, Mannheim, Germany

[21] Appl. No.: 104,160

[22] PCT Filed: Feb. 5, 1993

[86] PCT No.: PCT/DE93/00096

§ 371 Date: Aug. 20, 1993

§ 102(e) Date: Aug. 20, 1993

[87] PCT Pub. No.: WO93/16370

PCT Pub. Date: Aug. 19, 1993

[30] Foreign Application Priority Data

Feb. 5, 1992 [DE] Germany ............... 42 03 202.4

[51] Int. Cl.⁶ .................................................. G01N 21/35
[52] U.S. Cl. ................... 436/8; 436/171; 73/1 R; 73/61.48
[58] Field of Search ............... 422/82.09; 436/164, 436/8, 166, 171, 172; 250/252.1; 73/1 R, 61.48; 356/39, 433–436

[56] References Cited

U.S. PATENT DOCUMENTS

| | | | |
|---|---|---|---|
| 3,776,635 | 12/1973 | Haskell | 356/43 |
| 4,224,405 | 9/1980 | Hijikata | 435/3 |
| 4,660,151 | 4/1987 | Chipman et al. | 364/498 |
| 5,068,536 | 11/1991 | Rosenthal | 250/341 |

FOREIGN PATENT DOCUMENTS

| | | |
|---|---|---|
| 0210417 | 2/1987 | European Pat. Off. . |
| 2820441 | 11/1978 | Germany . |
| 3729189 | 3/1988 | Germany . |
| 3908831 | 9/1989 | Germany . |

*Primary Examiner*—Jeffrey R. Snay
*Attorney, Agent, or Firm*—Nikaido, Marmelstein, Murray & Oram

[57] ABSTRACT

A method for the analysis of a medical sample, particularly a body fluid, with the aid of an analyzing instrument, in which a test fluid, which contains an aliquot part of the sample and reagents, is in an optical cuvette and the temperature of the test fluid is determined in the cuvette. In order to determine the temperature of the test fluid directly and without contact, in a temperature calibration step the optical absorption of a calibrator fluid is determined at various temperatures at at least two wavelengths within the NIR range in order to obtain a calibration data set relating to the temperature-dependency of the optical absorption. In a temperature-measuring step the optical absorption of a test fluid of unknown temperature is measured at the same wavelengths and its temperature is determined by comparison of the absorption data obtained in the measuring step with the calibration data set.

11 Claims, 3 Drawing Sheets

METHOD FOR ANALYSIS OF A MEDICAL SAMPLE

The invention relates to a method and an instrument for the analysis of a medical sample, particularly a body fluid such as blood or urine.

The analysis is performed with the aid of reagents, enzymatic and immunochemical reagents being especially important. For the determination of a specific component of a body fluid (usually called a "parameter"), a specific set of reagents (such as, for example, enzymes, indicators or antibodies) and auxiliary materials (such as, for example, buffers, wetting agents and the like) are required, which are together called a reagent system for the determination of the particular parameter. The reagents are mixed with an aliquot part of the sample synchronously or in a plurality of stages one after the other, and incubated in order to allow the analytical reaction to occur.

At the end of the reaction a physically detectable change takes place, which is measured as a measurable variable that is characteristic of the sought-after concentration of the analyte. In most cases this is a colour change, which can be measured quantitatively with the aid of a photometer. However, other optical (e.g. nephelometric and fluorimetric) and non-optical (e.g. electrochemical) test principles are also used. The invention relates in particular to analyses in which the physically detectable change is measured by optical means, but is basically also suitable for other test principles.

The reactions which occur during these clinicochemical tests must in most cases take place at exactly pre-determined temperatures, the requisite temperature stability and accuracy frequently being given as plus/minus 0.1° C. Maintaining and controlling the temperature of test fluids in the reaction vessels of analysing instruments is therefore a problem with which those skilled in the art have long been occupied.

In many cases the reaction vessels are transported through the analysing instrument in a thermostatically controlled water bath. The good heat transfer associated with this gives rise to the fact that the reference temperature in the reagent vessels is reached relatively rapidly and is held satisfactorily constant. However, this solution to the problem is very expensive from the design point of view.

In the majority of analysing instruments, maintaining the desired temperature is therefore attempted using solid or gaseous media. In widespread use are designs in which the reaction vessels are located in recesses of rotors or transport magazines (so-called "racks"), the rotor or the rack being held at a defined temperature with the aid of temperature-measuring elements and heating devices, and the aim being to ensure the best possible heat transfer by accurate adjustment of the fit of the reaction vessel in the rotor or rack. However, this presupposes that the temperature of the reaction vessels is uniformly influenced by their temperature stabilisation in all positions of the rotor or rack. Practical experience shows that unavoidable temperature gradients lead to considerable differences between the actual temperature in the reaction vessel and the reference temperature. Similar problems also exist in the case of systems in which the reaction vessels are bathed in temperature-stabilised air.

In another known analysing instrument, the problem of unavoidable temperature gradients between the air surrounding the reaction vessels and the reaction vessels themselves is prevented in that a liquid crystal film is disposed on the wall of the reaction vessel and irradiated by a light source. The change in the reflected light as a function of temperature is detected and permits good accuracy of the temperature determination. The application of liquid crystals substantially increases the cost of the reaction vessels, which are in most cases single-use disposable plastic vessels. If the liquid crystal layer is applied on the outside, there remains a temperature gradient through the thermally relatively well insulating plastic wall of the reaction vessel to the fluid in its interior. If the liquid crystal is applied on the inside, problems can arise during mixing, and there is a risk of reactions of the liquid crystal with reagents of the reagent system.

The aim of the invention is therefore to provide a method of analysis and an analysing instrument in which the temperature of the test fluid can be determined directly and without contact in the test fluid itself.

The aim is achieved by a method for analysis of a medical sample with the aid of an analysing instrument in which, in an optical cuvette within the analysing instrument, there is a test fluid containing an aliquot part of the sample and reagents, which are at least a part of a specific reagent system for the analysis of the component, and the temperature of the test fluid is determined in the cuvette, the optical absorption of a calibrator fluid being determined in a temperature calibration step at various temperatures at at least two wavelengths within the NIR range in order to obtain a calibration data set relating to the temperature-dependence of the optical absorption, and the optical absorption of a test fluid of unknown temperature being measured in a temperature measuring step at the same wavelengths, and the temperature being determined by comparing the absorption data obtained in the measuring step with the calibration data set.

In the present invention, the determination of the temperature is based on the temperature-dependent change in optical absorption within the NIR range (800 nm to 2500 nm) of the electromagnetic spectrum. Within this spectral range there are absorption bands which are overtones and combination bands of various modes of oscillation of water. The temperature dependence of these absorption bands is very slight. The finding that, within the framework of clinicochemical analysis, NIR absorption measurements can be evaluated at justifiable (relatively small) cost for this field in such a way that the temperature in the reaction vessels can be determined with sufficient accuracy is therefore essential for the invention.

As mentioned above, the invention is suitable in particular for analysing instruments in which an optical absorption is determined as the physically detectable change. In this case, with expediency the wavelength-selective absorption-measuring device present in any case is also used to make the absorption measurements necessary for the temperature determination. In this arrangement, the temperature-measuring step can take place synchronously or in close time association with the absorption measurement necessary for the analysis, and in the same optical measuring cuvette. However, the wavelengths at which the absorption measurement for the analysis is made to differ from those at which the temperature determination is made. The former may also belong to other spectral ranges, in particular the range of visible light.

A good (low-noise) absorption-measuring signal is essential for the invention. A light source of sufficiently high intensity and a sensitive and stable optical sensor must therefore be used. The beam from the transmitter to the electromagnetic receiver should be as low-loss as possible.

To obtain the calibration data set, the absorption A (1, T) is measured as a function of the wavelength 1 and the temperature T. The temperatures for which a calibration measurement is made should be evenly distributed over the temperature range of interest.

The optical absorption in the temperature calibration step at each measuring point (i.e. for each calibrator fluid and each calibration temperature) is preferably measured a plurality of times at each measuring wavelength. The improvement in the measuring signal resulting from this multiple measurement and subsequent averaging of the measured values has proved very important for achieving good measuring accuracy. The number of measurements for each measuring point (and all wavelengths in each case) should be more than five, and preferably more than ten.

In the temperature measuring step also, a corresponding multiple measurement is preferably made in each test fluid whose temperature is to be determined, and for all measuring wavelengths. Here, the number of measurements can be smaller, but is similarly preferably more than five.

As regards the wavelengths, within the framework of the invention it was found possible to work with only two wavelengths. In this arrangement, using relatively simple mathematical methods a calibration line or simple calibration curve can be calculated from the absorption values obtained in the temperature calibration step, in this case the calibration data set being stored as coefficients of the equation of the calibration curve. However, more elaborate mathematical evaluation methods also enable the absorption spectra to be used in a broader spectral range or a spectral range with higher resolution for the temperature determination. In this case, during the temperature calibration step absorption spectra within the full NIR range or in one or a plurality of partial ranges thereof are recorded for a large number of temperatures. The calibration data thereby obtained are compressed using a mathematical regression method. For example, various methods of multivariate analysis are suitable within the framework of the invention. PLS (partial least square) regression in particular has proved suitable for practical purposes. Here, the numerous input variables are reduced to two relatively small matrices representing, for example, vectors and associated factors. These data are stored as a calibration data set. In the temperature measurement step, factors of the factor matrix are determined from the measured spectrum and the vector matrix. The temperatures are derived from this by comparison with the factor matrix of the calibration data set.

Details of these mathematical methods need not be described here, because they are known from the relevant literature. We refer in particular to the book written by H. Martens and T. Naes entitled "Multivariate calibration", John Wiley and Sons, 1991, pages 97 to 125, and to U.S. Pat. No. 4,660,151.

In respect of its optical absorption properties at the wavelengths used, the calibrator fluid used during the temperature calibration step must correspond with the test fluid whose (unknown) temperature is to be determined. In composition there are inevitable differences in that the test fluid contains an unknown concentration of the component to be analysed. Relative to the total quantity of the test fluid, however, these concentration differences are very small. Practical experiments have revealed that, within the framework of these concentration variations, the optical absorption properties change so little that the accuracy of the temperature determination is influenced thereby only very slightly. In order to minimise the influence of the sample it can, however, be expedient to use a set of calibrator fluids which contains the relevant sample constituents in their anticipated concentration range (i.e. the range of variation of the protein concentrations or turbidities, for example, is covered by the calibrator set).

The calibrator fluid used should preferably contain all constituents of the reagent system for the determination of the component to be analysed that are important for the optical absorption. Furthermore, if the material of the cuvettes in which the absorption of the test fluid is determined is not fully reproducible (above all when using single-use disposable cuvettes), in the calibration step also it is expedient to make a plurality of measurements in which the calibration fluid is in different cuvettes. Here, as explained in more detail below, the calibration step can be divided into two partial steps, the special influences mentioned being taken into account in the first step, while the second partial step concentrates on recalibration with a view to instrumental measuring errors.

The method according to the invention makes direct determination of the temperature of the fluid possible with practically no time delay (less than 1 second) or distortion of the measured value due to heat transfer. In this way the test fluid can be brought to the desired temperature very rapidly. The control constants of temperature control can be considerably shorter than in previously known methods. Methods can also be used in which the heat is produced directly within the test fluid, for example, heating with ultrasound or by infrared irradiation. Since the temperature of a plurality of cuvettes used in an analysing instrument can be individually controlled independently of one another, the temperature can be individually adjusted to the requirements of the particular test without problems.

In the most general embodiment of the invention, the physically measurable change which results from the reaction of the sample with the reagent system and is measured as the measurable variable which is characteristic of the analytical value of the sample, need not necessarily take place in the same optical cuvette as that in which the temperature-measuring step for the determination of the temperature of the test fluid is performed. For example, in an analytical method it may be necessary to monitor the temperature of a preliminary reaction, within the framework of the invention this preliminary reaction being permitted to take place in an optical cuvette, and the temperature of the test fluid contained therein being determined according to the invention. However, measurement of the measurable variable which is characteristic of the analysis, and the temperature determination with the aid of the temperature measuring step preferably take place in the same optical cuvette and at the same time (or with a small time difference). If the measurable variable is the optical absorption, then the wavelength at which the measurable variable is measured should differ from the wavelengths of the temperature-measuring step according to the invention.

If measurement of the measurable variable and the temperature determination according to the invention take place in the same optical cuvette, it can be advantageous to eliminate elaborate thermostatic regulation by measuring the measurable variable at a notexactly predetermined temperature and correcting the value of the measurable variable measured at a specific time by means of the temperature of the test fluid determined from absorption data essentially synchronously in a temperature-measuring step. Here "essentially synchronously" is to be understood as meaning that the time association is close enough to exclude impairment of the measuring accuracy by a temperature change taking place between the two measuring times.

This embodiment is especially important in the case of tests in which a reaction kinetics is determined as a measure of the concentration of the analyte in the sample. During the determination of enzyme concentrations, for example, the time change of a measurable variable (in most cases the optical absorption of the fluid at a specific wavelength) is usually determined. This is done by means of a series of measurements at successive times during which it is usually verified, by means of very complicated thermostatic regulation measures, that a desired reference temperature (in most cases 37° C.) is exactly adhered to throughout the whole measuring time of the kinetic measurement. Instead of this, within the framework of the present invention highly accurate thermostatic regulation can be dispensed with, i.e. it is accepted that the actual temperature in the optical cuvette differs from the desired reference temperature per se. By way of the practically delay-free measurement possible, according to the invention, at the exact site of the optical absorption measurement, the values of the measurable variable measured at a deviant actual temperature can be converted into corresponding values at the reference temperature, and these converted values can be used as the basis of further processing to the sought-after analytical value.

The conversion can be performed in various ways with the aid of the microcomputer technology now available. For example, a table or a functional relationship between the measurable variable and the temperature can be stored in a memory of the microcomputer for converting the measurable variable measured at the actual temperature into the corresponding value at the reference temperature for the particular parameter.

DE-B-28 20 441 describes how, for the case of kinetic determination of the rate of the enzymatic reaction which is also preferred within the framework of the present invention, the measured extinction values should be corrected with the aid of a temperature coefficient, which is continuously altered in dependence on the measured actual temperature. The actual temperature measurement is made using a thermoelement immersed in the cuvette. Here, if the intention is to determine the temperature in the same optical measuring cell as that in which the extinction measurement also takes place, the temperature-measuring sensor must be immersed in the optical cuvette and be withdrawn from it again prior to the extinction measurement, because it otherwise interferes with the optical measurement. However, as a result of this the measuring time of the temperature measurement and the measuring time at which the measurable variable is determined do not correspond exactly. Furthermore, fluid adhering to the temperature-measuring sensor is transferred from one cuvette to another ("carry-over"), and the inertia of the usual temperature measuring sensors is considerable. Conversely, if the temperature measurement is moved outside the optical beam, then the measuring site of the temperature measurement does not correspond to the measuring site of the extinction measurement. This too can result in distortions owing to temperature gradients. There is also the additional cost of the requisite exact temperature measurement.

However, within the framework of the present invention it is possible to determine the measurable variable (in particular an optical measurable variable) and the temperature in the same cuvette in very close association in respect of time (a few milliseconds) and space. In this way, in particular during the analysis of enzymes and other kinetic methods of analysis, a very high degree of accuracy is possible without the extremely complicated thermostatic regulation previously necessary in the case of methods of this type. Surprisingly, temperature determinations based on absorption measurement within the NIR range are possible practically synchronously with measurement of a time-variable absorption in the same sample taking place at another wavelength.

The invention is explained in more detail below by means of an exemplifying embodiment represented in the following figures:

Figure 1:
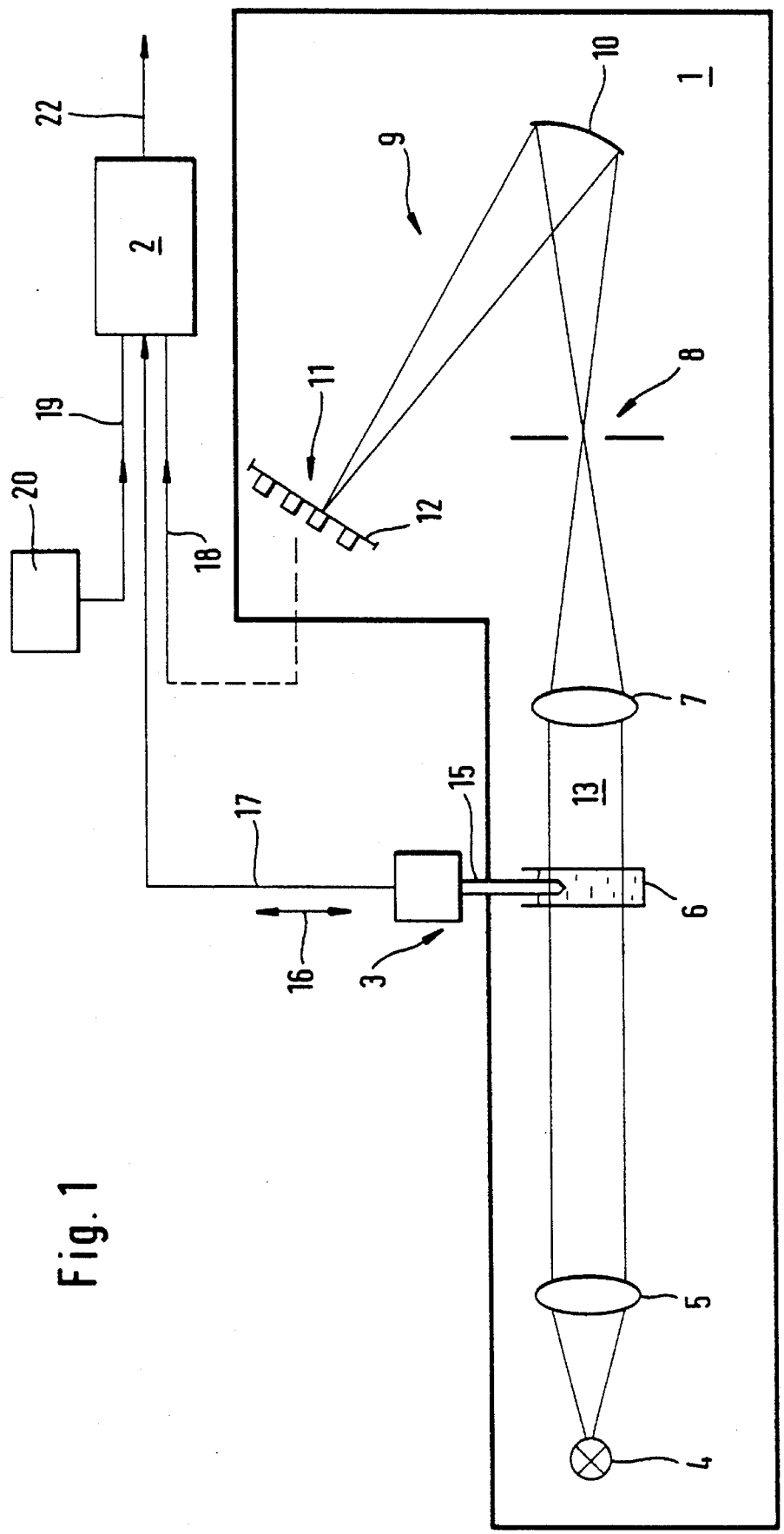
FIG. 1 A diagrammatic sketch of a device suitable for the invention.

The arrangement shown in FIG. 1 contains the essential elements necessary in order to determine the temperature in an analysing instrument from NIR absorption spectra, namely a wavelength-selective absorption-measuring device 1, a computer unit 2 and a temperature-measuring device 3.

The wavelength-selective absorption-measuring device 1 has the usual constituent parts of a spectral photometer, namely a transmitter 4 with a high intensity within the NIR range (e.g. a halogen lamp), an image-forming system consisting of lenses 5, 7 and a slit 8, an optical diffraction grating 10 and a receiver 11 which, in the case shown, is in the form of a detector strip 12 with a plurality of linearly disposed detectors. In this way, using a static diffraction grating 10 a spectrum can be recorded in more than one channel simultaneously.

Other selective absorption-measuring devices can also be used in place of the type shown. Of course it is possible to work with only one radiation receiver 11, which is rigidly positioned and receives in a single channel the spectrum which impinges on it from a swivel-mounted grating or prism. Furthermore, the wavelength-selection device of the absorption-measuring device need not allow continuous spectral diffraction (like a grating or prism). Rather, the requisite wavelength selectivity can also be achieved with filters and/or wavelength-selectively emitting light transmitters and/or light receivers.

In principle, therefore, various types of known spectralphotometer arrangements are suitable for the absorption-measuring device. In this arrangement it is, however, essential that the absorption spectrum produced has a good signal-to-noise ratio.

In the context of clinical chemistry, it is frequently necessary to analyse very small sample volumes. During experimental testing of the invention, for example, cuvettes with a fluid volume of less than 50 μl were used, whose measuring window was only 1×1 mm in size. Here, the use of a fibre-optic system has proved successful, in which the light is guided from the light transmitter to the cuvette using an optical fibre, and the light emerging from the cuvette is conducted to the measuring receiver using a second optical fibre. In this arrangement, by means of known micro-optical elements on the front faces of the optical fibres adjacent to the cuvette it is ensured that the light beamed through the cuvette from the first optical fibre enters the second optical fibre as totally as possible.

Within the beam path 13 of the measuring device, as usual there is a cuvette 6, which is filled with a fluid whose optical absorption is to be measured. It can be regarded as a special feature that a temperature-measuring device is envisaged which has a temperature sensor that is, or can be, disposed within the optical cuvette so that the temperature of a calibration fluid contained therein can be accurately determined during a wavelength-selective absorption measurement.

The practical realisation of this measure depends on the design characteristics of the particular analysing instrument. In the case shown, the temperature-measuring device 3 is vertically movable (arrow 16) in order to immerse the temperature sensor 15 from above in a cuvette 6 positioned within the beam path 13. This is possible above all in the case of those analysing instruments in which the optical absorption measurement necessary for the analysis takes place in the reaction vessels themselves. In this arrangement, the reaction vessels in most cases have a tubular shape with an at least partially square or rectangular cross-section and transparent walls, and are open at the top.

In cases in which it is not possible or expedient to immerse a temperature sensor 15 in the cuvette 6, a special temperature calibration cuvette in a movable mounting can be provided which is moved into the beam path 13 whenever a temperature calibration step is to be performed. Such a temperature-measuring cuvette can have a rigidly fixed temperature-measuring sensor on the inside. Alternatively, the beam path can also be turned towards a rigidly installed temperature-measuring cuvette.

The manufacture and introduction of the calibrator fluid necessary for the temperature calibration is possible without problems using the means commonly used in analysing instruments in order to prepare the reaction mixture. To this end, each analysing instrument has a so-called liquid-handling system consisting of stationary or movable pipettes, dispensers, stock bottles, hoses, pumps and the like, said liquid-handling system advantageously also being usable for the preparation of the temperature calibrator solution.

The temperature-measuring device 3 produces temperature-measuring signals which are fed via the cable 17 to the computer unit 2, to which via a cable 18 the signals from the receiver 11 of the absorption-measuring unit 1 are also fed. Via a third input cable 19, the computer is connected to a code-reading unit 20. The data is output from the computer unit 2 via an output cable 22 to a display which is not shown, or alternatively for further processing of the temperature-measuring data.

The temperature measurement according to the invention is made in two steps.

In the first instance, in the temperature calibration step the optical absorption of a calibrator fluid in a cuvette 6 is determined for at least two wavelengths, and preferably for a large number of wavelengths within a larger spectral range. This is repeated for a larger number of different temperatures evenly distributed over the temperature range of interest. In this arrangement, the temperature is in each case measured with the temperature sensor 15. The computer unit 2 records and stores the temperatures and the absorption values as a function of wavelength and temperature (A (1,T)). From this, a calibration data set is obtained in the computer unit 2 and stored.

As mentioned above, it is important for the invention that, in respect of their absorption properties, the calibrator fluid and the test fluid practically fully correspond at the measuring wavelengths. This is not easy to achieve in the case of analysing instruments, above all if the instrument is used for analysing different parameters for which completely different reagent systems are used. In this case, parameter-specific temperature calibration can be necessary, in which the calibration step is carried out separately for each component to be analysed, the calibrator fluid containing, in each case, all constituents of the reagent system which are important for the optical absorption, said reagent system being envisaged for the determination of the particular component.

In order to perform such a parameter-specific temperature calibration on the analysing instrument itself, it is necessary to keep stocks of the calibrator fluid suitable for each parameter, or to prepare said calibrator fluid case by case and, if the temperature of a test fluid is to be determined with the reagent system of this parameter, in each case to perform a parameter-specific calibration step. This necessitates an elaborate design of the analysing instrument and reduces its analytical performance, because temperature calibration steps must be performed relatively frequently.

For this reason, the temperature calibration step preferably takes place in the form of two partial-steps separated in space and time. A first partial step is, with expediency performed independently of the analysing instrument by the manufacturer of the reagent system in which a parameter-specific calibration data set is determined. This should be done separately for each production batch of a reagent system in order also to take account of production-determined differences in the temperature calibration between batches. The parameter-specific calibration data set thus obtained is delivered to the user of the analysing instrument in machine-readable form, for example as a magnetic code card, together with the reagent system and, with the aid of the code-reading unit 20 sent to the computer unit 2 via the cable 19.

This batch-specific, though instrument-independently performed temperature calibration can take the properties of the particular reagent fully into account. However, instrument-related sources of error such as, for example, production tolerances, drift, and variations of the absorption-measuring device are not included. For this reason, an additional parameter-neutral calibration step on the instrument is necessary, in which the optical absorption on a parameter-neutral calibrator fluid (for example water) is determined at at least one known temperature. In this arrangement, a calibrator fluid which has long-term stability is preferably used for the partial step of the temperature calibration taking place within the instrument, Said calibrator fluid is advantageously present in a sealed temperature-calibration cuvette with a rigidly integrated temperature-measuring sensor, and is in each case brought into the beam path for performance of the partial step. In some circumstances, instead of a calibrator fluid another calibrator medium, in particular air, can also be used in the second calibration step.

During the calibration step (or, if this is performed in two partial steps, in each of the partial steps) the temperature of the calibrator fluid or the calibration medium must, of course, be determined very exactly. The techniques necessary for this (high-precision temperature-measuring elements such as, for example, thermistors, a sufficiently high thermal capacity of the container, careful setting of the thermal equilibrium) are known.

During the temperature-measuring step, the optical absorption of the test fluid in the cuvette 6 is measured at the same wavelengths, and its temperature is determined by comparing the thereby measured absorption A (1) at unknown temperature T with the calibration data set. This comparison is performed in the computer unit 2 by usual data processing means, different mathematical methods (algorithms) being usable, as will hereinafter be illustrated using two examples.

Figure 2:
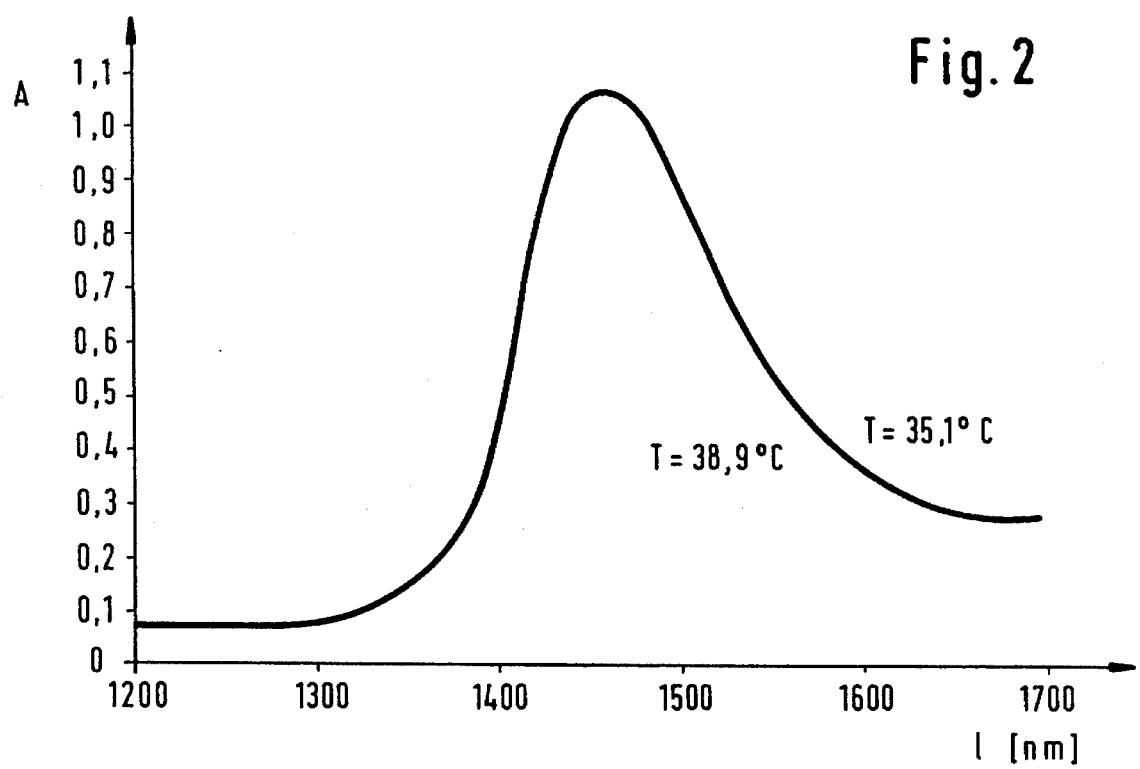
FIG. 2 and FIG. 3 The NIR spectrum of a sample at two different temperatures, FIG. 3 representing a sectional enlargement of FIG. 2.
Figure 3:
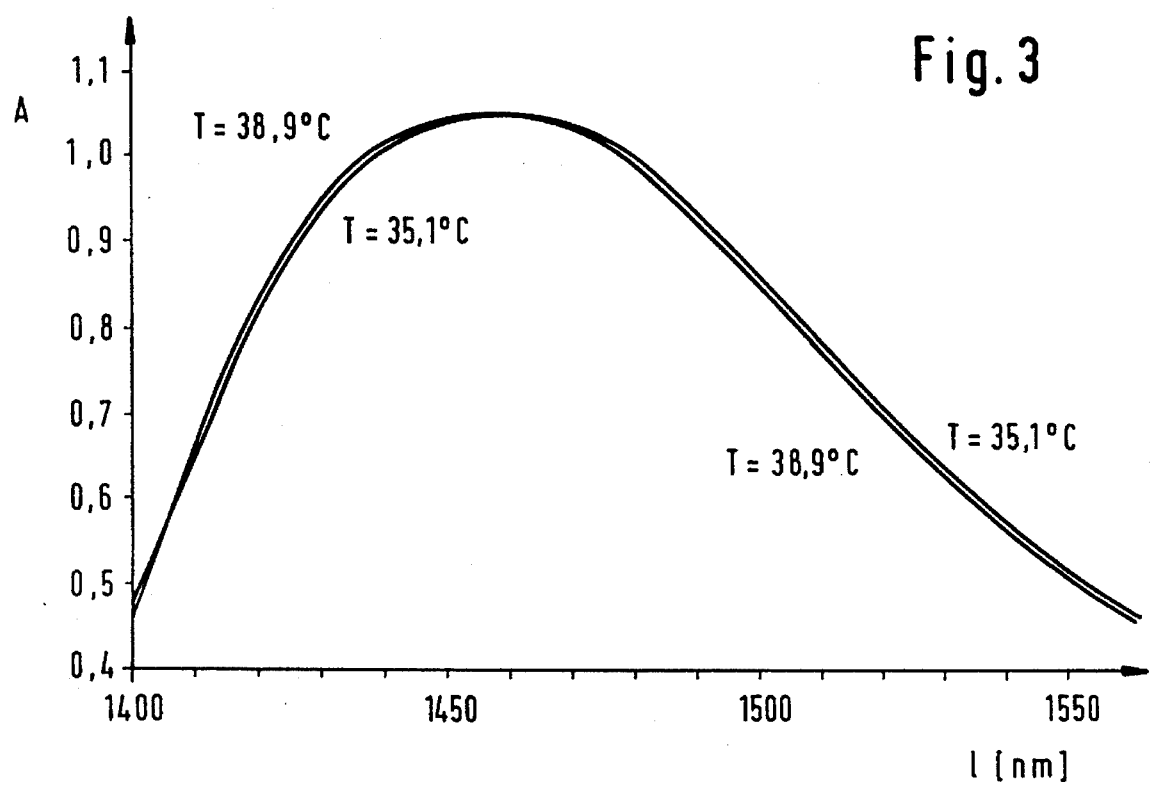

FIG. 2 and FIG. 3 show the absorption spectrum of a 10% solution of BSA (bovine serum albumin) at two different temperatures given in the figure. The difference is so small that it is discernible only from the sectional enlargement (FIG. 3).

Even so it was found that, even with the aid of absorption values at only two fixed wavelengths, a temperature determination is possible.

Of the BSA solution mentioned above, 36 spectra between about 1200 nm and 1700 nm were recorded at different temperatures which were roughly evenly distributed within the range 35° C. to 39° C. Here, the temperature in the cuvette was determined using an NTC resistor, with the use of a non-linear calibration curve a standard deviation of the NTC-temperature measurement of 0.02° C. being achieved. In the case of the spectral photometer used, the whole spectrum was digitalised into 266 wavelengths (i.e. each spectrum comprised the absorption values for 266 wavelengths within the spectral range under investigation).

These calibration data were fitted to a bilinear calibration equation of the general formula:

$$T = C_o + C_1 A_1 + C_2 A_2 \quad (1)$$

In the course of this, all 35,245 different combinations of two of the 266 different wavelengths were calculated for the bilinear calibration. The wavelength combination with the smallest standard deviation was used as the calibration data set for the determination of unknown temperatures.

The optimal combination was the wavelengths 1405 nm and 1534 nm with the calibration equation $$T = .96° C. + .78° C. \times A_{1405nm} - 165.81° C. \times A_{1534nm} \quad (2)$$

Figure 4:
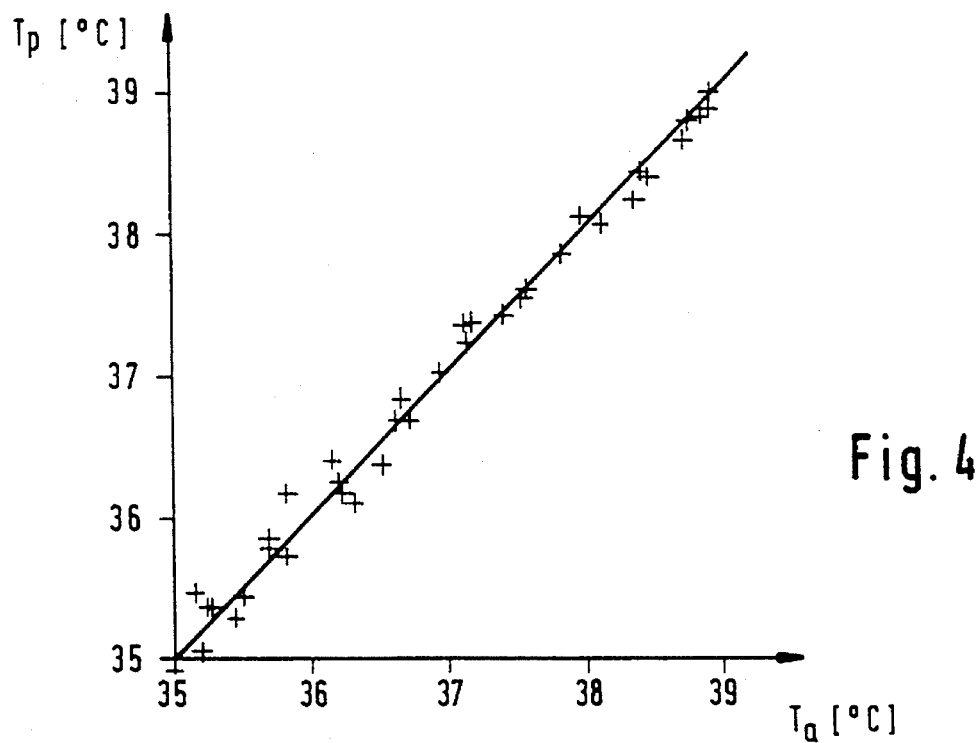
FIG. 4 and FIG. 5 Graphical representations of the measuring results for two different embodiments of the invention.

The results of the temperature determination are shown in FIG. 4.

Here, the temperature $T_p$ calculated from the absorption values of two wavelengths with the aid of equation (2) is plotted against the temperature $T_a$ measured with the NTC. The measuring points are scattered evenly around the line, which has a gradient of 1. The standard deviation is 0.14° C.

In this example, the wavelengths were selected using a statistical method. Comparison with FIG. 2 and FIG. 3 shows that the wavelength 1405 nm lies on the short-wave flank of the absorption band, and the wavelength 1534 nm on the long-wave flank. Since the temperature-dependence of the absorption has opposite signs on the two flanks of the absorption band (FIG. 3), this choice of wavelengths, together with the formation of the differential, leads to a stronger temperature-measuring signal. It is also important that, by the differential formation, all additive measuring errors are eliminated.

It can also be advantageous to define the wavelengths at which the optical absorption is measured, so that one wavelength lies within an absorption band of water and a second wavelength lies outside the absorption bands of water. In this way also, by establishing the differential between the two absorption values, a relatively strong temperature-measuring signal can be achieved with the suppression of additive contributions to the error.

Figure 5:
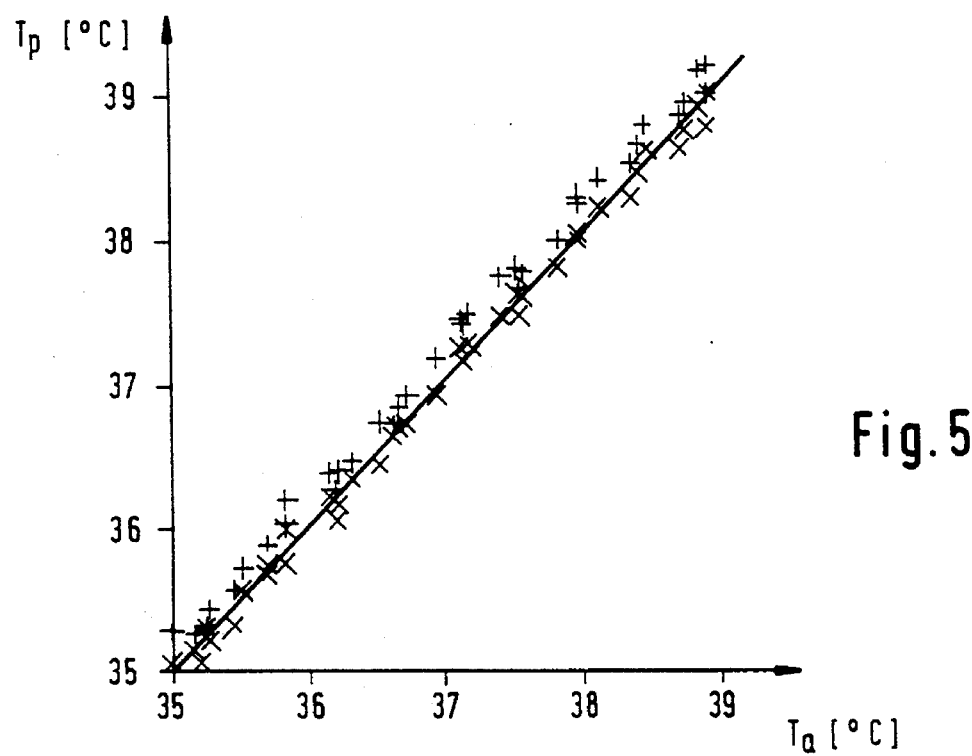

FIG. 5 shows the results obtained from the same calibration and measuring data using another mathematical method of comparison, namely PLS regression (as an example of multivariate analysis). Here, 36 calibration spectra were each used for all 266 wavelengths. The + symbols mark the results of a PLS analysis with two factors, and the × symbols the results of an analysis with three factors. When three factors were taken into account, the standard deviation was 0.08° C.

As expected, the use of complete spectra with the aid of multivariate analysis gives a better correlation and thus a better accuracy of the temperature determination than if only two fixed wavelengths are used. However, since analysing instruments are in practice often fitted with spectral photometers which are able to measure at only a small number of fixed wavelengths, the realisation that knowledge of the spectrum within a broader spectral range is not absolutely necessary is especially important. It is sufficient if the absorption device anyhow present is modified so that the absorption at the wavelengths within the NIR range, which are necessary for the temperature determination, can be determined.

Overall it is shown that, even in the presence of a critical interference substance such as BSA, which strongly influences absorption and is typical of test systems in medical analysis, the temperature of a test fluid can be determined from the absorption spectra with an astonishingly high degree of accuracy.

In other experiments, the invention was tested experimentally under additionally complicated marginal conditions. Disposable minicuvettes whose measuring window was only 1×1 mm in size were used. The length of the optical path within the cuvette was 5 mm, and its volume was 50μl.

In these cuvettes text mixtures were investigated comprising conventional reagent systems for the determination of magnesium, cholesterol, creatinine and triglycerides and different protein concentrations (corresponding to practically occurring values). Here, the above-mentioned analytical parameters are selected so that the reagent systems contain especially critical constituents, for example a high protein content, a pigment which absorbs in the long-wave range, a high salt content, or overall an especially complex reagent composition.

The absorption measurements in the calibration step and in the temperature-measuring step were made in separately prepared test mixtures at wavelengths between 1030 nm and 1390 nm, in new disposable cuvettes in each case.

The calibration was performed parameter-specifically, the calibrator fluid in each case containing the whole reagent system, but no serum protein. During the calibration, the temperature was varied in steps of 0.1° (in some cases 0.2°) within the range 35° C. to 39° C., in each case 50 measurements over the entire wavelength range ("scans") being made with a wavelength resolution of 32 cm$^{-1}$ or, in the case of the triglyceride test, 64 cm$^{-1}$. The calibration data were processed using a PLS regression method. The optimum number of factors in the PLS matrix was determined by cross-validation, and was four for creatinine and triglycerides, and five for magnesium and cholesterol.

During the temperature-measuring step in test mixtures of unknown temperature, eight or eleven scans were made with a resolution of 32 cm$^{-1}$, and thirteen scans with a resolution of 64 cm$^{-1}$. Here, the measuring time was less than five seconds in each case.

With a conventional FT-NIR spectrometer and using a commercially available PLS algorithm (LabCalc PLSPlus, from Galactyc Industries), for the different reagent systems the standard deviations in ° C obtained between the conventionally measured temperature and the temperature determined according to the invention are as follows:

TABLE 1

| Reagent system | Standard deviation (°C.) |
|---|---|
| Magnesium | 0.071 |

TABLE 1-continued

| Reagent system | Standard deviation (°C.) |
|---|---|
| Cholesterol | 0.083 |
| Creatinine | 0.078 |
| Triglycerides | 0.069 |

Overall this shows that, even under the complicated marginal conditions described, the temperature can be determined with an accuracy better than 0.1° C.

We claim:

1. A method for analysis of a liquid medical sample with the aid of an analysis instrument, said method comprising:

an analytical measurement step for the determination of a measurable variable, said measurable variable being characteristic of an analytical value of the sample in an optical cuvette, said cuvette containing a test fluid, said test fluid comprising an aliquot part of the sample and reagents which are a part of a reagent system which is specific for the analysis of the sample, said analytical measurement step comprising reacting the sample and the reagents to cause a measurable temperature dependent change in the test fluid, and measuring said measurable change as the measurable variable;

a temperature measuring step wherein an optical absorption of said test fluid of unknown temperature is measured in the optical cuvette by irradiating the test fluid with at least two wavelengths within the NIR-range between 800 nm and 2500 nm, and the temperature is determined by comparing absorption data obtained in the temperature measuring step with a calibration data set relating to a temperature dependence of the optical absorption of the test fluid, said calibration data set being generated in a temperature calibration step in which the optical absorption of a calibrator fluid, different from the test fluid and having a known temperature, is determined at various temperatures at at least two wavelengths.

2. Method according to claim 1, wherein the optical absorption in the temperature calibration step is measured a plurality of times on a specific calibrator fluid and at a specific temperature.

3. Method according to claim 1, wherein the optical absorption in the temperature-measuring step is measured a plurality of times on a test fluid for the determination of a temperature value.

4. Method according to claim 1, wherein the wavelengths at which the optical absorption is measured include one wavelength on the short-wave and one on the long-wave flank of an absorption band of water.

5. Method according to claim 1, wherein the wavelengths at which the optical absorption is measured include a wavelength within an absorption band of water and a wavelength outside the absorption bands of water.

6. Method according to claim 1, wherein a multivariate analysis is performed to compare the calibration data set obtained in the temperature calibration step with the absorption data obtained in the temperature-measuring step.

7. Method according to claim 1, wherein the sample is analysed for a plurality of different components (parameters) and, for the determination of a parameter-specific calibration data set, the calibration step is carried out separately for each component to be analysed, the calibrator fluid containing, in each case, all constituents of the reagent system required for the determination of the particular component which are important for the optical absorption.

8. Method according to claim 7, wherein the calibration step includes two partial steps, in a first partial step, which is performed independently of the analysing instrument, the parameter-specific calibration data set being determined, and in a second partial step within the analysing instrument the optical absorption on a parameter-neutral calibration medium being determined for at least one known temperature in order to obtain additionally parameter-neutral calibration data.

9. Method according to claim 1, wherein the analytical measurement step is performed at an approximately predetermined temperature, an a temperature adjustment of the measurable variable is performed by means of the temperature of the test fluid determined in the temperature-measuring step.

10. Method according to claim 9, wherein the measurable variable is the optical absorption of the test fluid and the optical absorption of the test fluid is determined in the analysis mesurement step at at least one wavelength which is different from the wavelengths of light used in the temperature measuring step and the temperature calibration step.

11. Method according to claim 9, wherein the measurable variable is measured on a test fluid a plurality of times in sucession and the temperature adjustment is carried out in order to determine the time dependent change of the measurable variable at a reference temperature as a measure of reaction kinetics.

* * * * *